(12) United States Patent
Zhang et al.

(10) Patent No.: US 7,665,355 B2
(45) Date of Patent: Feb. 23, 2010

(54) DOWNHOLE SEAL ASSEMBLY HAVING EMBEDDED SENSORS AND METHOD FOR USE OF SAME

(75) Inventors: Haoyue Zhang, Dallas, TX (US); Michael L. Fripp, Carrollton, TX (US); Doug Beck, Calgary (CA)

(73) Assignee: Halliburton Energy Services, Inc., Houston, TX (US)

( * ) Notice: Subject to any disclaimer, the term of this patent is extended or adjusted under 35 U.S.C. 154(b) by 128 days.

(21) Appl. No.: 11/729,746

(22) Filed: Mar. 29, 2007

(65) Prior Publication Data

US 2008/0236271 A1 Oct. 2, 2008

(51) Int. Cl.
*E21B 44/00* (2006.01)
(52) U.S. Cl. .................................. 73/152.48
(58) Field of Classification Search .............. 73/152.48; 166/250.01, 250.17
See application file for complete search history.

(56) References Cited

U.S. PATENT DOCUMENTS

| | | | | |
|---|---|---|---|---|
| 4,089,927 A | * | 5/1978 | Taylor | 310/331 |
| 4,426,884 A | * | 1/1984 | Polchaninoff | 73/172 |
| 6,316,084 B1 | | 11/2001 | Claus et al. | 428/212 |
| 6,691,788 B1 | | 2/2004 | Dearing | 166/382 |
| 6,896,049 B2 | | 5/2005 | Moyes | 166/82.1 |
| 7,234,517 B2 | * | 6/2007 | Streich et al. | 166/66 |
| 2004/0060696 A1 | * | 4/2004 | Schultz et al. | 166/250.01 |
| 2004/0065436 A1 | | 4/2004 | Schultz et al. | 166/250.01 |
| 2004/0112597 A1 | | 6/2004 | Hamid et al. | 166/250.17 |

FOREIGN PATENT DOCUMENTS

EP 1 428 975 A1 6/2004

OTHER PUBLICATIONS

Baker Oil Tools develops expandable sealing technology; http://www.bakeroiltools.com; (admitted prior art).
Nano Sonic, Inc.; Metal Rubber™ Sensors and Electrodes (Product #: MR-01-D5- and MR-01-S5); products@nanosonic.com; (admitted prior art).

* cited by examiner

*Primary Examiner*—Hezron Williams
*Assistant Examiner*—Tamiko D Bellamy
(74) *Attorney, Agent, or Firm*—Lawrence R. Youst

(57) ABSTRACT

A downhole seal (50) includes an elastomeric element (98) operably to provide a seal between two downhole components. A strain sensor (102) is embedded in the elastomeric element (98). The strain sensor (102) has a mechanical flexibility that is substantially matched to the mechanical flexibility of the elastomeric element (98). The strain sensor (102) is operably connected to circuitry that is operable to identify changes in a property of the strain sensor (98) indicative of the strain being experienced by the strain sensor (98), which is representative of the strain experienced by the elastomeric element (98).

20 Claims, 6 Drawing Sheets

DOWNHOLE SEAL ASSEMBLY HAVING EMBEDDED SENSORS AND METHOD FOR USE OF SAME

TECHNICAL FIELD OF THE INVENTION

This invention relates, in general, to a downhole seal assembly for providing a seal between a production tubular and a wellbore during the production of oil, gas or water and, in particular, to a downhole seal assembly having embedded sensors that are used to monitor strain within the downhole seal assembly.

BACKGROUND OF THE INVENTION

Without limiting the scope of the present invention, its background will be described with reference to producing fluid from a subterranean formation, as an example.

After drilling each of the sections of a subterranean wellbore, individual lengths of relatively large diameter metal tubulars are typically secured together to form a casing string that is positioned within each section of the wellbore and cemented in place. This casing string is used to increase the integrity of the wellbore by preventing the wall of the hole from collapsing and to prevent movement of fluids from one formation to another formation.

After well construction is finished, the completion process begins. The completion process comprises numerous steps that include creating hydraulic openings or perforations that extend through the production casing string and the cement, as well as a short distance into the desired formation or formations, so that production fluids can enter the interior of the wellbore. In addition, the completion process may involve formation stimulation to enhance production, installation of sand control devices to prevent sand production and the like. The completion process also includes installing a production tubing string within the well casing. Unlike the casing string that forms a part of the wellbore itself, the production tubing string is used to produce the well by providing the conduit for formation fluids to travel from the formation depth to the surface.

Typically, the production tubing string extends from the surface to the formations traversed by the well and includes one or more production seal assemblies. The purpose of the seal assemblies is to support the production tubing and other completion equipment and to seal the annulus between the outside of the production tubing and the inside of the well casing to block movement of fluids through the annulus past the seal assembly locations. Commonly, multiple seal assemblies are utilized within a tubing string such that multiple formations or multiple zones within a formation can be isolated from one another. Such isolation allows formation or zone specific treatment regimens to be performed. In addition, such isolation allows more precise control over the production from the well.

A number of problems may occur during the installation and use of traditional seal assemblies. For example, the elastomeric material in the seal assembly can extrude into undesired regions due to high stress, faulty design or extreme wellbore conditions. In addition, other problems associated with traditional seal assemblies include premature setting, incomplete setting and loss of long term sealing capacity.

To overcome these and other problems associated with traditional seal assemblies, test wells and laboratory facilities are commonly used to perform testing of seal assembly designs. For example, in order to perform certain testing of the mechanical operation and responses of a seal assembly design, the seal assemblies are placed inside a section of well casing for testing. While valuable information can be obtained using such testing methods, aspects of the mechanical response of the elastomeric elements within a seal assembly remain difficult to directly observe. In addition, it has been found that the temperatures and the large deformations to which the elastomeric seal elements are subjected do not allow the use of traditional strain sensors. Specifically, available strain sensors are limited by maximum temperature, maximum strain or both.

Therefore, a need has arisen for a system and method of monitoring the mechanical response of the elastomeric elements within a downhole seal assembly during installation and operation of the downhole seal assembly. A need has also arisen for such a system and method wherein the sensors used to monitor the mechanical response of the elastomeric elements can withstand the temperatures and strains encountered in the downhole operating environment of the downhole seal assembly. Further, a need has arisen for such a system and method of monitoring the mechanical response of the elastomeric elements within a downhole seal assembly during the design and testing of downhole seal assemblies.

SUMMARY OF THE INVENTION

The present invention disclosed herein comprises a downhole seal assembly containing one or more embedded sensors that provide for the monitoring of the mechanical response of the elastomeric elements of the seal assembly during installation and operation as well as during design and testing. The embedded sensors used in the downhole seal assembly of the present invention can withstand the temperatures and strains encountered in the downhole operating environment of the downhole seal assembly. The monitoring capability of the embedded sensor is achieved by matching the mechanical flexibility of the embedded sensors to the mechanical flexibility of elastomeric elements of the seal assembly while providing an electrical or magnetic property that varies according to the strain experienced by the sensor.

In one aspect, the present invention is directed to a downhole seal that comprises an elastomeric element operable to provide a seal between two downhole components. A strain sensor is embedded in the elastomeric element. The strain sensor has a mechanical flexibility that is substantially matched to the mechanical flexibility of the elastomeric element. The strain sensor is operably connected to circuitry that is operable to identify changes in a property of the strain sensor indicative of the strain being experienced by the strain sensor.

In one embodiment, the strain sensor includes alternating layers of an inorganic material and an organic material. In this embodiment, the inorganic material is electrically conductive and may be selected from the group consisting of metals and metal oxides. Also, in this embodiment, the organic material may be selected from the group consisting of polymers and elastomers. In another embodiment, the strain sensor is formed from multiple oppositely charged layers of at least a first and a second material held together by electrostatic charges.

In one embodiment of the downhole seal, the circuitry identifies changes in an electrical property of the strain sensor such as the resistance, the capacitance or the dielectric permittivity of the strain sensor as an indication of the strain being experienced by the strain sensor. In another embodiment, the circuitry identifies changes in a magnetic property of the strain sensor, such as the magnetic permittivity of the strain sensor as an indication of the strain being experienced by the strain sensor.

In another aspect, the present invention is directed to a downhole seal assembly that includes a tubular element having first, second and third elastomeric seal elements disposed thereabout and is operable to provide a seal between the tubular element and a wellbore. A setting assembly is disposed about the tubular element and is operable to actuate the first, second and third elastomeric seal elements from a non-sealing position to a sealing position. A strain sensor is embedded in at least one of the first, second and third elastomeric elements. The strain sensor has a mechanical flexibility that is substantially matched to the mechanical flexibility of the elastomeric element in which the strain sensor is embedded. Circuitry is electrically connected to the strain sensor. The circuitry is operable to identify changes in an electrical property of the strain sensor indicative of the strain being experienced by the strain sensor.

In one embodiment of the downhole seal assembly, the strain sensor is embedded in at least one of the first and the third elastomeric elements to detect strain concentrations near a point of contact with the setting assembly. In another embodiment, the strain sensor is embedded in the second elastomeric element to detect extrusion of the second elastomeric element under at least one of the first and the third elastomeric elements.

In a further aspect, the present invention is directed to a method for determining sealing characteristics of a downhole seal assembly. The method includes embedding a first strain sensor at a first location in an elastomeric element of the downhole seal assembly, wherein the mechanical flexibility of the first strain sensor is substantially matched to the mechanical flexibility of the elastomeric element, disposing the downhole seal assembly in a wellbore, setting the downhole seal assembly in the wellbore, detecting a change in a property of the first strain sensor and determining the strain at the first location based upon the change in the property of the first strain sensor, thereby determining a first sealing characteristic of the downhole seal assembly.

The method may also include embedding a second strain sensor at a second location in the elastomeric element of the seal assembly, detecting a change in a property of the second strain sensor and determining the strain at the second location based upon the change in the property of the second strain sensor, thereby determining a second sealing characteristic of the downhole seal assembly.

In one implementation, the step of determining the strain at the first location based upon the change in the property of the first strain sensor further comprises determining that the seal assembly is not fully set due to the strain at the first location being below a predetermined level. In another implementation, the step of determining the strain at the first location based upon the change in the property of the first strain sensor further comprises determining that the seal assembly is not properly set due to the strain at the first location being above a predetermined level.

The present invention also provides for modifying the design of the downhole seal assembly based upon strains identified in the seal assembly using embedded sensors. For example, a plurality of strain sensors may be embedded at respective locations within or on the surface of the elastomeric element or elements of a downhole seal assembly. Thereafter, changes in a property in each of the strain sensors are detected to determine the localized strain at each of the respective locations based upon the detected changes in the property of the strain sensors. The design of the downhole seal assembly may then be modified based upon the localized strains.

BRIEF DESCRIPTION OF THE DRAWINGS

For a more complete understanding of the features and advantages of the present invention, references now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention, and do not delimit the scope of the invention.

Figure 1:
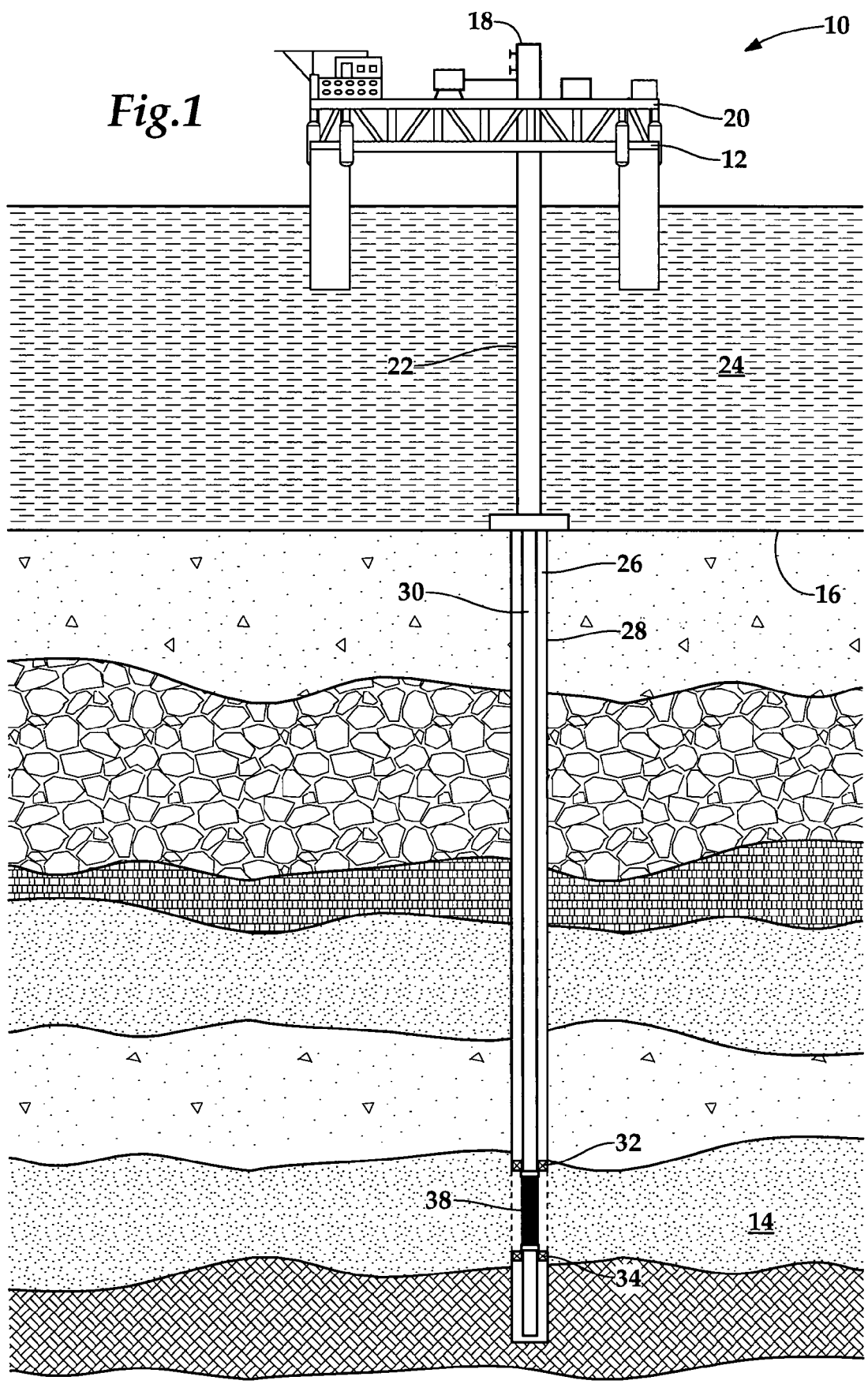
FIG. 1 is a schematic illustration of an offshore oil and gas platform operating a pair of downhole seal assemblies having embedded strain sensors according to the present invention.

Referring now to FIG. 1, an offshore oil and gas production platform operating a pair of seal assemblies having embedded strain sensors is schematically illustrated and generally designated 10. A semi-submersible platform 12 is centered over a submerged oil and gas formation 14 located below sea floor 16. Wellhead 18 is located on deck 20 of platform 12. Well 22 extends through the sea 24 and penetrates the various earth strata including formation 14 to form wellbore 26. Forming the interior surface of wellbore 26 is a casing 28. Disposed within casing 28 and extending from wellhead 18 is production tubing 30. During production, formation fluids enter wellbore 26 through perforations in casing 28 and travel into tubing 30 to wellhead 18, entering tubing 30 through sand control screen 38. A pair of seal assemblies 32, 34 provide a seal between tubing 30 and casing 28 to prevent the flow of production fluids therebetween. According to the present invention, seal assemblies 32, 34 contain embedded strain sensors that measure the strain in the elastomeric elements of seal assemblies 32, 34. Information from these embedded sensors can provide desirable information about the condition of the seal assemblies as well as the quality of the seal being provided. For example, if the magnitude of the strain experienced by one of the elastomeric elements of one of the seal assemblies does not reach a predetermined value, there is a likelihood that the seal assembly is incompletely set. As another example, which is of particular importance in open hole completions in lateral or horizontal wellbores, differing strain values on circumferentially opposite sides of the seal assembly can indicate that the seal assembly is not providing a complete circumferential seal.

Even though FIG. 1 depicts a cased well, it should be understood by those skilled in the art that the seal assemblies with embedded sensors of the present invention are equally well suited for use in open hole or uncased wells. Therefore, when a seal assembly having embedded sensors of the present invention is described as providing a seal against a wellbore, it is to be understood that the wellbore may be cased or uncased. Even though FIG. 1 depicts a vertical wellbore, it should be understood by those skilled in the art that the seal assemblies with embedded sensors of the present invention are equally well suited for use in horizontal or deviated wellbores. Accordingly, it should be understood by those skilled in the art that the use of directional terms such as above, below, upper, lower, upward, downward and the like are used in relation to the illustrative embodiments as they are depicted in the figures, the upward direction being toward the top of the corresponding figure and the downward direction being toward the bottom of the corresponding figure. Even though FIG. 1 depicts an offshore operation, it should be understood by those skilled in the art that the seal assemblies with embedded sensors of the present invention are equally well suited for use in onshore operations.

Figure 2A:
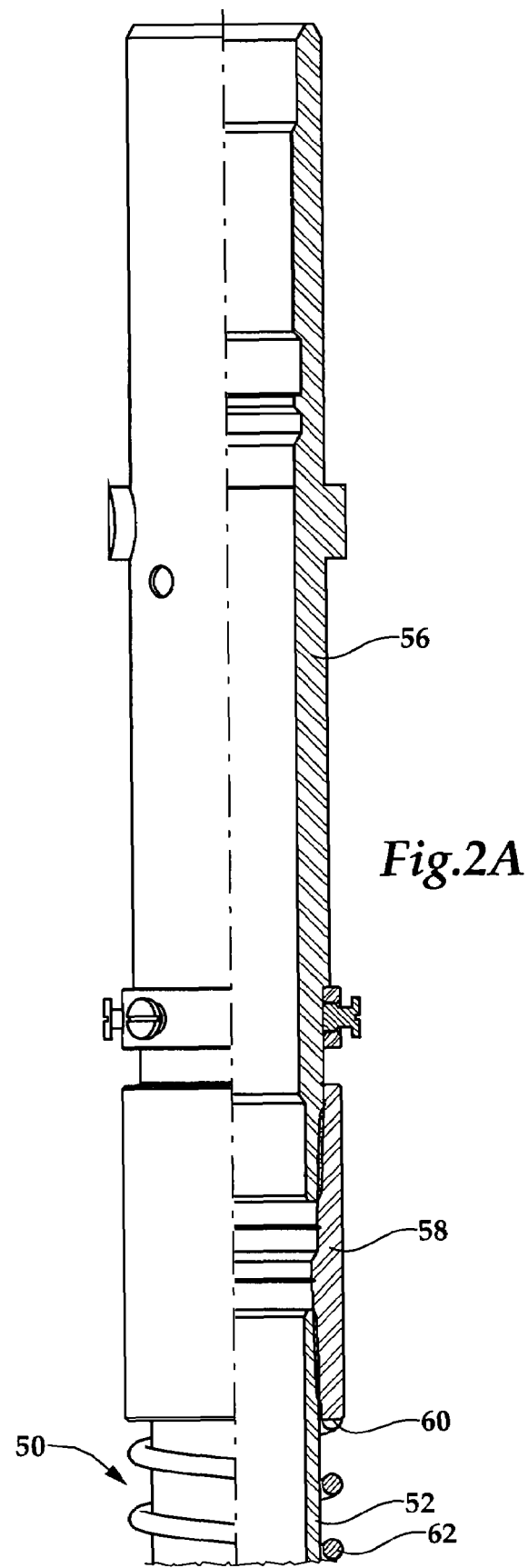
FIGS. 2A-2C are axial views in quarter section of a retrievable downhole seal assembly having embedded strain sensors according to the present invention.
Figure 2B:
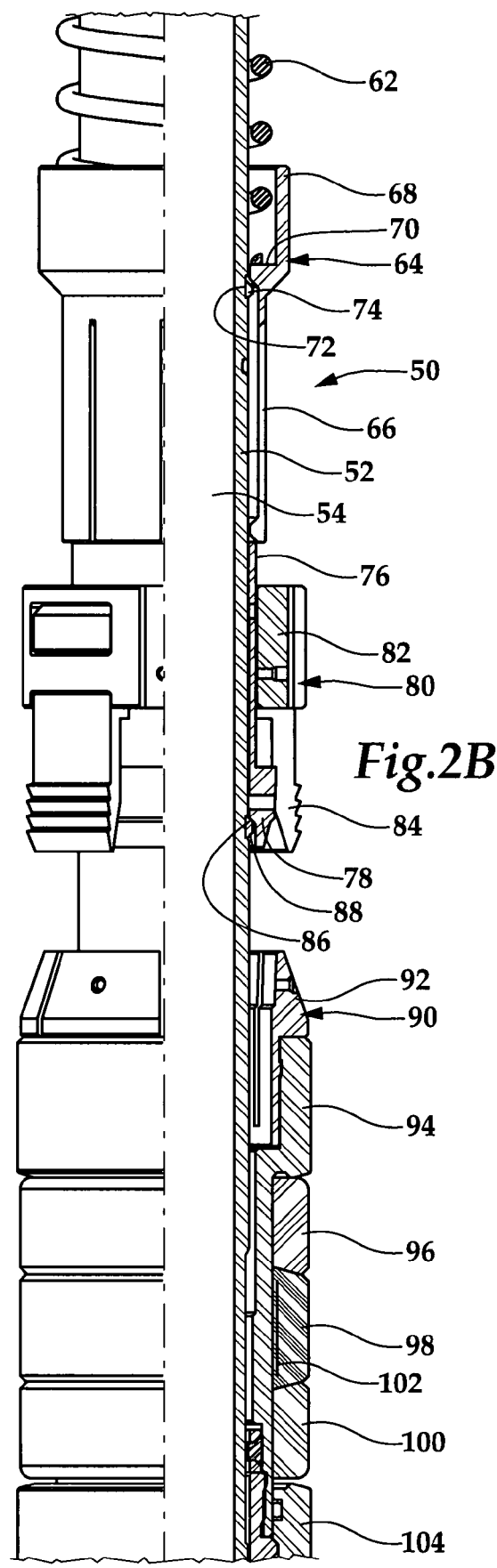
Figure 2C:
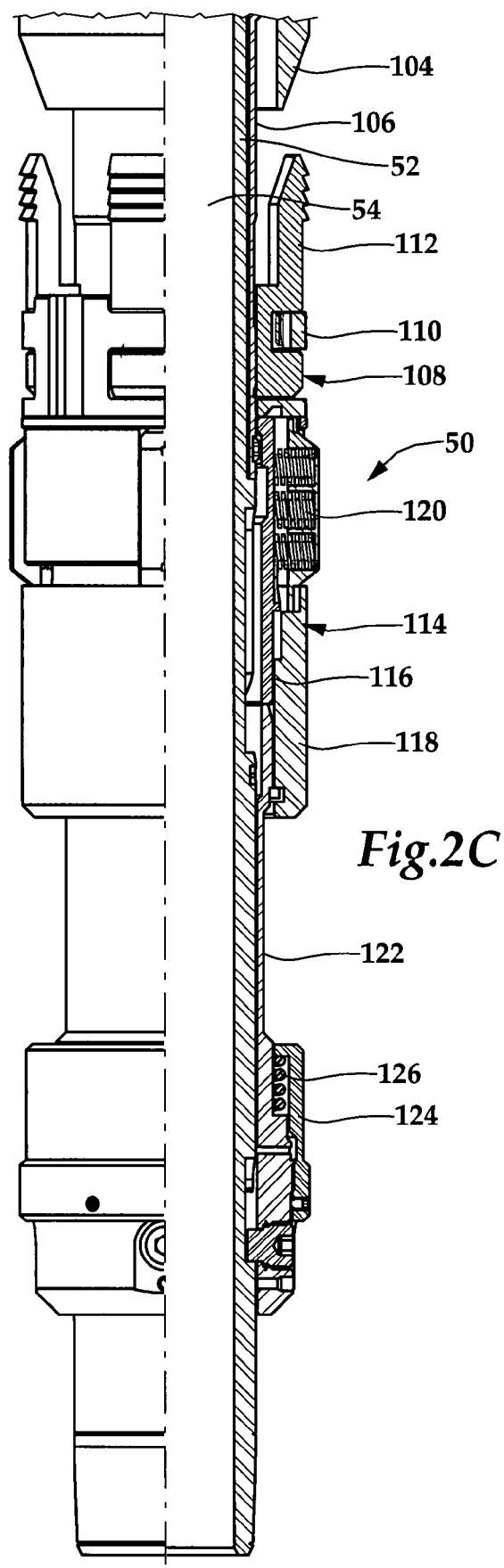

Referring now to FIG. 2, including FIGS. 2A-2C, therein is depicted a seal assembly having embedded sensors of the present invention that is generally designated 50. Seal assembly 50 includes a substantially tubular, longitudinally extending mandrel 52 having a substantially cylindrical bore 54 defining a longitudinal production flow passageway. Mandrel 52 is coupled to a substantially tubular, longitudinally extending section of tubing 56 by a coupling 58. Coupling 58 includes a radially outwardly extending shoulder 60. Positioned around mandrel 52 is a spiral wound compression spring 62 that is operated against shoulder 60 of coupling 58.

Slidably positioned around mandrel 52 is a collet member 64. In the illustrated embodiment, collet member 64 includes eight collet fingers 66. As should be apparent to one skilled in the art, collet member 64 may have other numbers of collet fingers 66. In the illustrated embodiment, collet member 64 also includes a spring cover 68 that extends upwardly to cover a portion of spring 62. It should be understood by those skilled in the art that collet member 64 could alternatively have a spring cover that entirely covers spring 62 or could have no spring cover associated therewith. Collet member 64 has an upper shoulder 70 that is in contact with the lower end of spring 62 such that spring 62 downwardly biases collet member 64.

Positioned around mandrel 52 in a groove 72 is a snap ring 74 that initially prevents collet member 64 from moving downwardly relative to mandrel 52. A support ring 76 is slidably disposed around mandrel 52 below collet fingers 66 of collet member 64. Support ring 76 has radially expanded end portion 78. Slidably positioned around support ring 76 is a slip assembly 80. Slip assembly 80 includes a slip carrier 82 and, in the illustrated embodiment, four radially extendable slips 84. As should be apparent to one skilled in the art, slip assembly 80 may have a variety of configurations including configurations having other numbers of slips 84, such configurations being considered within the scope of the present invention. Slips 84 each have a gripping outer surface for engaging and gripping the interior of the well casing in which seal assembly 50 is disposed. Positioned around mandrel 52 in groove 86 is a snap ring 88 that initially prevents support ring 76 and slip assembly 80 from moving downwardly relative to mandrel 52.

Slidably positioned around mandrel 52 at a preselected distance below support ring 76 and slip assembly 80 is a slip wedge 90. In the illustrated embodiment, slip wedge 90 includes six wedge sections 92. As should be apparent to one skilled in the art, slip wedge 90 may have a variety of configurations including configurations having other numbers of wedge sections 92, such configurations being considered within the scope of the present invention. Wedge sections 92 each have a camming outer surface that will engage the inner surface of slips 84. The interior surface of wedge sections 92 has a mating profile that matches the mating profile on the outer surface of support ring 76 such that support ring 76 can be received in the recess between wedges sections 92 and mandrel 52.

Securably attached to slip wedge 90 and slidably positioned around mandrel 52 is a mandrel element 94. In the illustrated embodiment, three elastomeric seal elements 96, 98, 100 are positioned around mandrel element 94. Any of elastomeric seal elements 96, 98, 100 may contain one or more embedded sensors according to the present invention. In the illustrated embodiment, elastomeric seal element 98 contains embedded sensor 102. Sensor 102 is formed from a conductive elastomer, discussed in greater detail below, and is embedded in elastomeric seal element 98. Circuitry, not shown in this illustration, is connected to one or more conductive layers within sensor 102 to detect a property of sensor 102, such as an electrical property or a magnetic property including resistance, capacitance, dielectric permittivity, magnetic permittivity or the like. The conductive elastomer from which sensor 102 is formed has a mechanical flexibility that is matched to the mechanical flexibility of the elastomer from which seal element 98 is manufactured. The matching of mechanical flexibility between sensor 102 and seal element 98 reduces the stress at the interface between sensor 102 and elastomeric seal 98 and reduces the risk of delamination that has plagued prior attempts to provide sensors embedded in elastomeric seal elements of seal assemblies. Accordingly, matching of the mechanical flexibilities of sensor 102 and seal element 98 does not require equality of the mechanical flexibilities but rather having mechanical flexibilities that are similar enough to substantially prevent delamination during the intended use of sensor 102. In certain embodiments, the mechanical flexibility of sensor 102 may be substantially matched to the mechanical flexibility of seal element 98. For example, the mechanical flexibility of sensor 102 may be up to about 25% greater than the mechanical flexibility of seal element 98. In other embodiments, the mechanical flexibility of sensor 102 may be up to about 25% less than the mechanical flexibility of seal element 98. Although only one elastomeric seal element in this illustrated embodiment contains an embedded sensor, this is by way of illustration only and is not a limiting feature of the present invention. In fact, each of the elastomeric seal elements of the seal assemblies of the present invention preferably includes numerous embedded sensors positioned at strategic locations within and on the surfaces of the elastomeric seal elements to provide strain information from throughout the elastomeric seal elements.

Slidably and sealing positioned around mandrel element 94 below seal element 100 is a slip wedge 104 that has a camming outer surface. When a compressive force is generated between mandrel element 94 and slip wedge 104, seal elements 96, 98, 100 are radially expanded into contact with the well casing. Coupled to the lower end of mandrel element 94 and slidably positioned around mandrel 52 is a mandrel element extension 106.

Slidably positioned around mandrel element extension 106 at a preselected distance below slip wedge 104 is a slip assembly 108. Slip assembly 108 includes a slip carrier 110 and, in the illustrated embodiment, four radially extendable slips 112. As should be apparent to those skilled in the art, slip assembly 108 may have a variety of configurations including configurations having other numbers of slips 112, such configurations being considered within the scope of the present invention. Slips 112 have gripping outer surfaces for engaging and gripping the interior of the well casing in which seal assembly 50 is disposed. Slips 112 each have an inner surface that engages the camming surface of slip wedge 104.

Positioned around mandrel 52 below slip assembly 108 is a drag block assembly 114. Drag block assembly 114 includes a drag block mandrel 116, a retainer 118 and four spring mounted drag blocks 120. As should be apparent to those skilled in the art, drag block assembly 114 may have a variety of configurations including configurations having other numbers of drag blocks 120, such configurations being considered within the scope of the present invention. Partially disposed within retainer 118 and slidably disposed around mandrel 52 is sleeve 122. Sleeve 122 has a housing 124 positioned around its lower end with a spring 126 positioned therebetween.

The operation of seal assembly 50 is now described. Once seal assembly 50 is attached within a work string, seal assembly 50 is run downhole and located in the desired position within the well casing. A gripping and sealing relationship is established between the seal assembly 50 and the well casing by mechanically shifting seal assembly 50. Specifically, mandrel 52 of seal assembly 50 is moved downwardly relative to slip assembly 108. Initially, slip wedge 104 travels with mandrel 52 until the camming surface of slip wedge 104 engage the inner surface of slips 112, which causes slips 112 to move radially outwardly into gripping engagement with the well casing.

Once slips 112 are set, mandrel 52 continues its downward travel which is now relative to not only slip assembly 108 but also to slip wedge 90, mandrel element 94, seal elements 96, 98, 100 and slip wedge 104. At this time, collet member 64, support ring 76 and slip assembly 80 continue to travel with mandrel 52 until the radially expanded end portion 78 of support ring 76 engages the inner surface of wedges sections 92 of slip wedge 90. Specifically, as the bias force of spring 62 is acting downwardly on collet member 64, collet fingers 66 positively operate against support ring 76 such that the radially expanded end portion 78 of support ring 76 slides between slip wedge 90 and mandrel 52.

Figure 3:
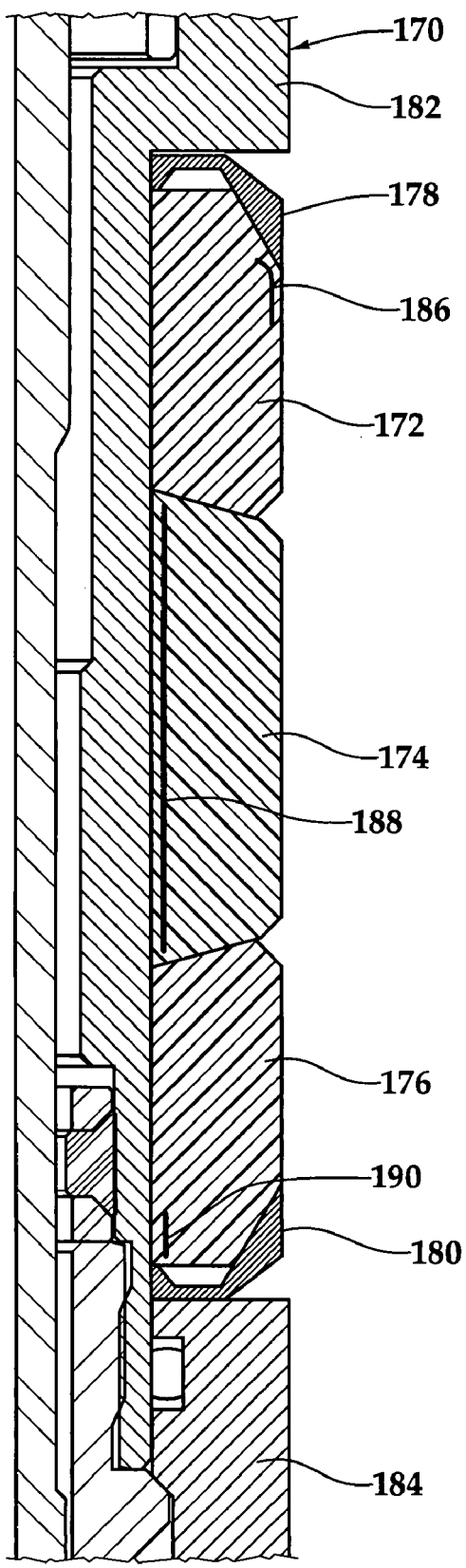
FIG. 3 is a cross-sectional view of the elastomeric seal elements of a downhole seal assembly having embedded strain sensors according to the present invention, with the seal assembly in an unset configuration.

Continued downward travel of mandrel 52 now compresses seal elements 96, 98, 100 between mandrel element 94 and slip wedge 104 into a sealing engagement with the well casing due to the transmission of the spring force via collet member 64, support ring 76 and slip wedge 90. When the spring force reaches a sufficient level, for example, 50 to 75 percent of the maximum spring force, collet fingers 66 radially outwardly expand over the upper end of support ring 76 and come in contact with slip carrier 82. Once collet fingers 66 contact slip carrier 82, the spring force now downwardly operates on slip carrier 82 causing the inner surfaces of slips 84 to engage the camming surfaces of wedge sections 92 of slip wedge 90, which causes slips 84 to move radially outwardly into gripping engagement with the well casing. In addition, the upper end of support ring 76 is contacted by snap ring 74. This configuration of seal assembly 50 represents the set position in which seal assembly 50 has a sealing and gripping relationship with the well casing Referring now to FIG. 3, a seal assembly having embedded sensors according to the present invention is depicted in the unset position and is generally designated 170. Seal assembly 170 includes elastomeric seal elements 172, 174 and 176, which are positioned between backup shoes 178, 180 and on the outer radial surface of mandrel element 182. A portion of mandrel element 182 is also positioned behind backup shoe 178. A slip wedge 184 is positioned behind backup shoe 180. In the illustrated embodiment, the outer two elastomeric seal elements 172 and 176, are formed of an elastomer that has a greater mechanical stiffness or lower mechanical flexibility than the elastomer used to form seal element 174. Sensors according to the present invention are embedded in each of elastomeric seal elements 172, 174 and 176. As illustrated, embedded within elastomeric seal element 172 is a sensor 186, embedded within elastomeric seal element 174 is a sensor 188 and embedded within elastomeric seal element 176 is a sensor 190. Certain issues associated with each of these sensor locations will be discussed below with reference to the elastomeric elements in a set position.

Each of sensors 186, 188 and 190 is made of a conductive elastomer. Sensors 186, 188 and 190 can be formed either as flat sheets or ropes of the conductive elastomer. The conductive elastomer contains very thin layers of an elastomeric material alternating with very thin layers of a conductive material, such as a metal or metal oxide, and will be described in greater detail below. The components of the elastomeric layers and the conductive layers can be modified when the conductive elastomer is manufactured, allowing the properties of the sensor to be matched to the desired use. For example, sensors 186 and 190 may contain a stiffer elastomeric material than sensor 188, so that each strain sensor is matched to the mechanical flexibility of the specific elastomer in which that sensor will be embedded.

The strain experienced by each of embedded sensors 186, 188 and 190 is separately monitored by circuitry, not shown, which detects changes in a property, such as an electrical or magnetic property, of the conductive elastomer. For example, in certain embodiments, the resistance experienced across sensors 186, 188 and 190 may vary according to the amount of deformation experienced by the sensor as elastomeric seal elements 172, 174 and 176 are deformed under the compressive forces exerted by mandrel element 182 and slip wedge 184. Other electrical properties may alternatively or additionally be affected and can be measured, such as the capacitance, the dielectric permittivity or the like. Similarly, magnetic properties may be affected and can be measured such as magnetic permittivity and the like.

Figure 4:
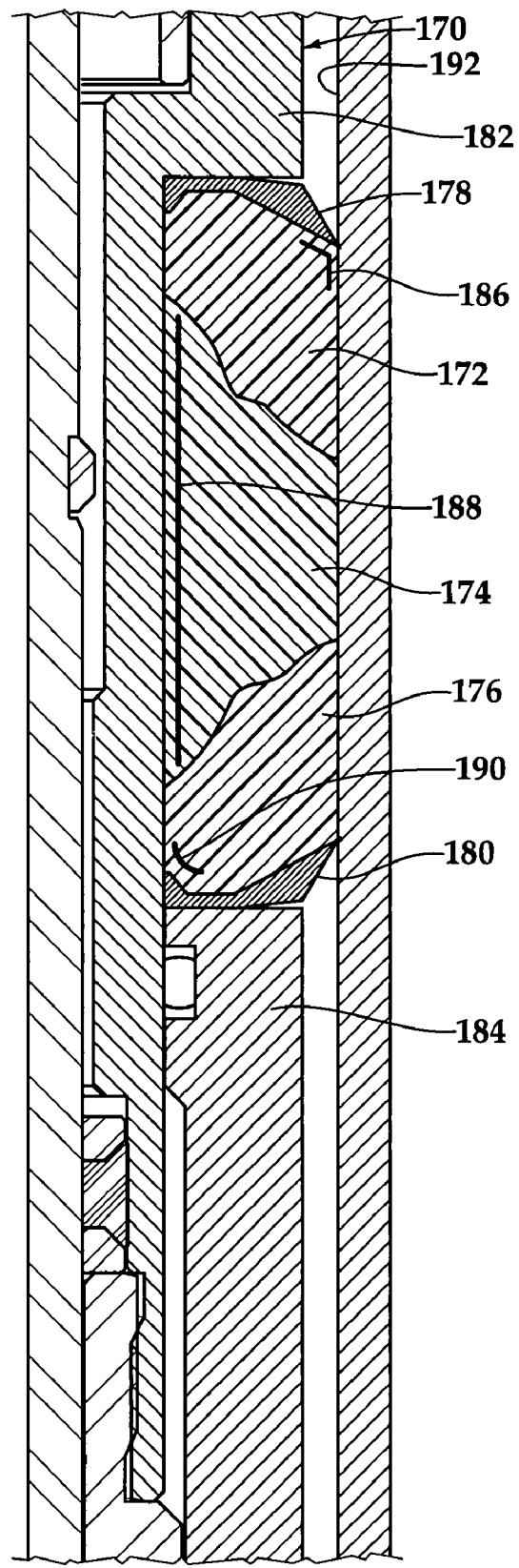
FIG. 4 is a cross-sectional view of the elastomeric seal elements of a downhole seal assembly having embedded strain sensors according to the present invention, with the seal assembly in a set configuration.

Referring now to FIG. 4, seal assembly 170 is depicted in its energized or set position. As shown, elastomeric seal elements 172, 174 and 176 have been compressed longitudinally by slip wedge 184 and mandrel element 182. As elastomeric seal elements 172, 174 and 176 are compressed, they have expanded in the radial direction until they provide a seal against the interior surface of the wellbore, which is illustrated as casing 192. As elastomeric seal elements 172, 174 and 176 are deformed, their respective sensors 186, 188 and 190 are also deformed which cause a change in one or more of their respective properties. By embedding sensors 186, 188 and 190 at appropriate locations within and on the surface of elastomeric seal elements 172, 174 and 176, potential problem areas can be monitored and problems detected at an early stage.

For example, one problem that can be encountered by seal assembly 170 is the tendency for elastomeric seal element 174 to creep under elastomeric seal elements 172 and 176. Excessive creep of elastomeric seal element 174 can hinder the expected operation of seal assembly 170 and may prevent an adequate seal from being established and maintained. In the illustrated embodiment, sensor 188 is placed proximate the inner radial surface of elastomeric seal element 188 to monitor the amount of strain at this location, which is representative of the amount of creep experienced by elastomeric seal element 188.

As another example, during the setting process, backup shoes 178 and 180 impinge on the exterior surface of seal elements 172 and 176 potentially causing seal elements 172 and 176 to expand beyond the outer radial edges backup shoes 178 and 180. This contact produces strain concentration in the elastomeric material that is adjacent the contact points. In the illustrated embodiment, sensor 186 is positioned at or near the point of contact with backup shoe 178 to monitor this high region of strain.

Likewise, during the setting process as backup shoes 178 and 180 compress seal elements 172 and 176, the inner radial portions of seal elements 172 and 176 can potentially extrude into any gap between backup shoes 178 and 180 and mandrel element 182. In the illustrated embodiment, sensor 190 is placed at this location in order to monitor the possibility of such extrusion.

Figure 5:
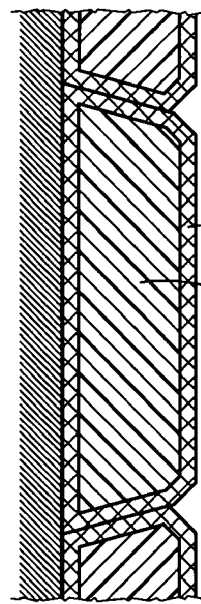
FIG. 5 is a cross-sectional view of an elastomeric seal element according to an embodiment of the present invention.

Referring now to FIG. 5, an elastomeric seal element 220 is shown according to an alternate embodiment of the present invention. In this embodiment, elastomeric seal element 220 contains a central core 222 comprising an elastomer. Conductive elastomer 224 forms an outer layer that completely covers seal element 220. In this embodiment, an electrical or magnetic property across the entire surface of elastomeric seal element 220 can be measured.

Figure 6:
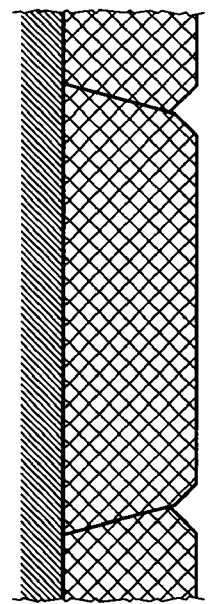
FIG. 6 is a cross-sectional view of an elastomeric seal element according to another embodiment of the present invention.

With reference now to FIG. 6, an elastomeric seal element 230 is shown according to an alternate embodiment of the present invention. In this embodiment, elastomeric seal element 230 is formed entirely or substantially entirely from the conductive elastomer. In this configuration, an electrical or magnetic property of the elastomeric seal element as a whole can be monitored.

Figure 7:
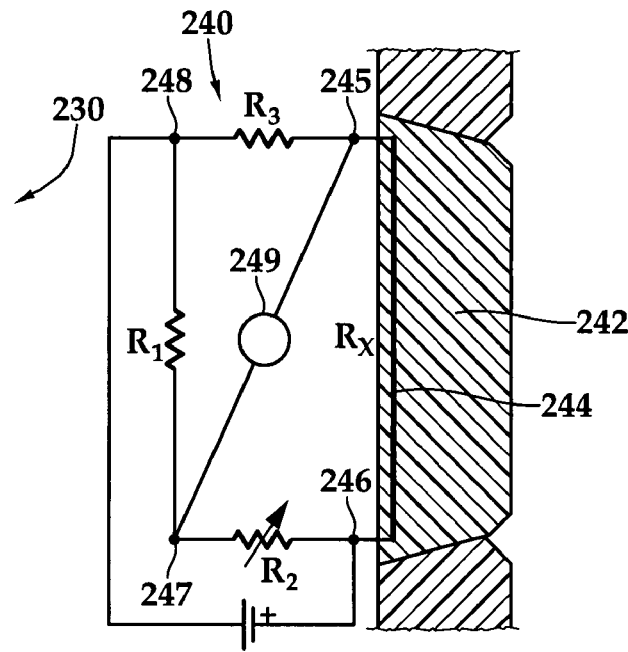
FIG. 7 is a view of a circuit attached to a strain sensor embedded in an elastomeric seal element according to the present invention.

With reference now to FIG. 7, one embodiment of circuitry used to measure the changes in resistance of an embedded strain sensor according to the present invention is shown and generally designated 240. Elastomeric seal element 242 contains embedded sensor 244, which is formed of a conductive elastomer. As elastomeric seal element 242 is placed under stress, the resultant strain causes both seal element 242 and strain sensor 244 to be deformed, which in turn causes changes in the resistance $R_x$ of sensor 244. Circuit 240 is attached to embedded sensor 244 at points 245 and 246 to measure resistance $R_x$. Points 245 and 246 are then part of a loop that includes points 247 and 248. A current source, such as a battery is connected to this circuit at points 246 and 248, while points 245 and 247 are connected to each other through a galvanometer 249 to measure the current therebetween. One skilled in the art will recognize that circuit 240 forms a Wheatstone bridge. In the Wheatstone bridge, resistances $R_1$, $R_2$, $R_3$ are known. When the ratio $R_2/R_1$ is equal to the ratio $R_x/R_3$ the voltage between points 245, 247 is zero and no current flows therebetween. When the ratio $R_2/R_1$ is not equal to the ratio $R_x/R_3$, the amount and direction of current that flows between points 245, 247 is measured by galvanometer 249 and is used to determine the value of $R_x$, which in turn is a reflection of the strain experienced by strain sensor 244. One of skill in the art will recognize that other circuits can also be used to measure the resistance across the conductive layers of sensor 244. Likewise, other electrical or magnetic properties of sensor 244 can be measured using other circuits known to those skilled in the art.

The measurements described are obtained for each strain gauge separately and can be transmitted to the surface or stored for retrieval by surface technologies. In at least one embodiment, a battery is used to power the transmissions. Transmission of strain sensor results does not need to be continuous. Instead, a signal can be sent at periodic intervals to conserve battery power and provide long-term coverage. In an alternate embodiment, sensor 244 shares a circuit with an antenna such that the frequency transmitted from the antenna varies with the resistance through sensor 244. Another alternative method of communicating the sensor information uses a passive circuit downhole. When the circuit is pinged with a broad frequency signal, the resonance from the circuit can be detected and analyzed to determine the strain in sensor 244.

Figure 8:
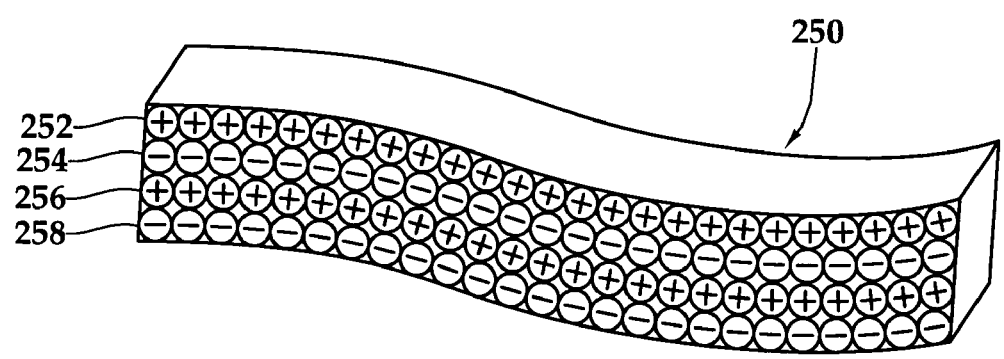
FIG. 8 shows a cross-section through a sheet of conductive elastomeric material that is used to form an embodiment of an embedded strain sensor of the present invention.

With reference now to FIG. 8, an embodiment of the conductive elastomer used in the disclosed embedded sensors is illustrated and the creation of this material is discussed. In the embodiment shown, conductive elastomer 250 is formed of layers 252, 256 of positively charged particles alternating with layers 254, 258 of negatively charged particles. Positively charged layers 252, 256 are conductive layers and are formed of inorganic materials such as metals or metal oxides. Negatively charged layers 254, 258 are formed of organic molecules, such as polymers or elastomers. Each layer is tightly bound to the adjacent layers by their opposing charges. Together, these layers form a material with the elasticity of an elastomer and the conductivity of a metal. Although the embodiment shown contains only four layers for illustration, the conductive elastomeric material used to make the embedded strain sensors of the present invention contains many more layers than are shown. Additionally, although the illustration discloses a material whose upper surface is of positively charged particles and whose lower surface is of negatively charged particles, one skill in the art would recognize that the outer surfaces of the conductive polymer can both be formed of either negatively charged particles or positively charged particles.

The conductive elastomer 250 is created by a process of electrostatic self-assembly, which in at least one embodiment, can be conducted at room temperature. To begin, a substrate, such as glass, is cleaned to remove surface impurities and to create a region of net charge at the molecular surface of the substrate. This net charge can be either negative or positive, depending on the substrate and the first layer to be assembled. For the sake of discussion, the net charge is assumed to be negative in the present embodiment. The substrate is immersed in a water-based solution containing positively charged ions. These positively charged ions can include metals and metallic oxides, such as $AL_2O_3$, $TiO_2$, $ZrO_2$, $SiO_2$, $Al_2O_3/SiO_2$, $Al_2O_3/ZrO_2$, $ZrO_2/SiO_2$ or $C_{60}$. The positively charged ions will self-assemble into layer 252, which adheres to the negative net charge on the substrate. The particles that form layer 252 do not necessarily form a pure compound, but can be a collection of molecules and atoms. Layer 252 may have electrical, magnetic or other types of properties that are different from those of their constituent atoms or molecules. These properties can be altered by controlling the size and morphology of the particles that constitute the solution from which layer 252 is assembled.

After the positively-charged ions have formed layer 252, the substrate is removed from the positively charged solution and rinsed thoroughly with water. The substrate is then immersed in a second water-based solution that contains negatively charged particles of an elastomeric compound. The elastomeric compound can be altered as desired to obtain the desired properties in the finished product. Layer 254 self-assembles from the negatively charged particles, forming a tight, organized layer of negatively charged molecules that are bonded to layer 252 by their opposing charges. After layer 254 forms, the substrate is removed from the negatively charged solution and thoroughly rinsed. The process of alternately immersing the substrate in a positively charged solution, rinsing, immersing in a negatively charged solution and rinsing continues until a material of the desired thickness is built up on the substrate. The final step removes the conductive elastomeric material from the substrate, giving material 250 shown in FIG. 8.

Conductive elastomer 250 has the flexibility and resilience of an elastomer and the conductivity of a metal. Additionally, because of the tight bonds, the conductivity is not destroyed by stretching or harsh treatment. Although the process of creating a conductive elastomer has been described in terms of forming a sheet of material, the conductive elastomer can also be formed on the exterior surface of an object, such as elastomeric seal element 220 of FIG. 5. The only requirement is the ability to form an initial net charge on the surface of the material.

Although the use of embedded sensors has been described in terms of monitoring the strain in a seal assembly that has been placed in service in a downhole completion, the embedded strain sensors of the present invention are also useful in monitoring the elastomeric elements of a seal assembly during the design of new seal assemblies. Current development relies heavily on known designs and modification by trial and error. Using the disclosed embedded sensors in the elastomeric elements of seal assemblies and other sealing devices, accurate information can be obtained about the weaknesses of a design without the need for visible signs of failure. With multiple sensors in different locations, additional information can be obtained during testing. Using this information, undesirable results can be evaluated so that improvements are incorporated into redesign efforts.

As shown in the discussion above, sensors formed of conductive elastomeric materials now provide the capability to monitor the strain in elastomeric seal elements that are used downhole under conditions of extreme stress and high temperatures. These sensors have both the flexibility of elastomers and the conductivity of metals. Unlike previous attempts to monitor downhole seal assemblies, the mechanical flexibility of the conductive elastomeric sensors can be matched to that of the elastomeric elements that the sensors monitor, reducing the problems previously encountered and increasing the information that can be collected.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A downhole seal comprising:
    an elastomeric element operably to provide a seal between two downhole components;
    a strain sensor embedded in the elastomeric element, the strain sensor having a mechanical flexibility that is substantially matched to the mechanical flexibility of the elastomeric element; and
    circuitry operably connectable to the strain sensor, the circuitry operable to identify changes in a property of the strain sensor indicative of the strain being experienced by the strain sensor.

2. The downhole seal as recited in claim 1 wherein the strain sensor further comprises alternating layers of an inorganic material and an organic material.

3. The downhole seal as recited in claim 2 wherein the inorganic material is electrically conductive.

4. The downhole seal as recited in claim 2 wherein the inorganic material is selected from the group consisting of metals and metal oxides.

5. The downhole seal as recited in claim 2 wherein the organic material is selected from the group consisting of polymers and elastomers.

6. The downhole seal as recited in claim 1 wherein the strain sensor further comprises multiple oppositely charged layers of at least a first and a second material held together by electrostatic charges.

7. The downhole seal as recited in claim 1 wherein the strain sensor is embedded within an elastomeric element of a downhole seal assembly operable to provide a seal between a production tubing and a wellbore.

8. The downhole seal as recited in claim 1 wherein the circuitry identifies changes in an electrical property of the strain sensor as an indication of the strain being experienced by the strain sensor.

9. The downhole seal as recited in claim 1 wherein the circuitry identifies changes in a magnetic property of the strain sensor as an indication of the strain being experienced by the strain sensor.

10. A downhole seal assembly comprising:
    a tubular element;
    first, second and third elastomeric seal elements disposed about the tubular element and operable to provide a seal between the tubular element and a wellbore when in a sealing position, the second seal element being disposed between the first and third seal elements;
    a setting assembly disposed about the tubular element and in contact with the first and third elastomeric seal elements, the setting assembly operable to actuate the first, second and third elastomeric seal elements from a non-sealing position to the sealing position;
    a strain sensor embedded in at least one of the first, second and third elastomeric elements, the strain sensor having a mechanical flexibility that is substantially matched to the mechanical flexibility of the elastomeric element in which the strain sensor is embedded; and
    circuitry electrically connectable to the strain sensor, the circuitry operable to identify changes in an electrical property of the strain sensor indicative of the strain being experienced by the strain sensor.

11. The downhole seal assembly as recited in claim 10 wherein the strain sensor further comprises alternating layers of a metal and an elastomeric material.

12. The downhole seal assembly as recited in claim 10 wherein the strain sensor is embedded in at least one of the first and the third elastomeric elements to detect strain concentrations near a point of contact with the setting assembly.

13. The downhole seal assembly as recited in claim 10 wherein the strain sensor is embedded in the second elastomeric element to detect extrusion of the second elastomeric element under at least one of the first and the third elastomeric elements.

14. A downhole seal comprising:
    an elastomeric element operably to provide a seal between two downhole components;

a strain sensor embedded in the elastomeric element, the strain sensor formed of a conductive elastomer having multiple oppositely charged conductive and nonconductive material layers held together by electrostatic charges, the strain sensor having a mechanical flexibility that is substantially matched to the mechanical flexibility of the elastomeric element; and circuitry operably connectable to the strain sensor, the circuitry operable to identify changes in a property of the strain sensor indicative of the strain being experienced by the strain sensor 15. The downhole seal as recited in claim 14 wherein the strain sensor further comprises alternating layers of an inorganic material and an organic material.

16. The downhole seal as recited in claim 15 wherein the inorganic material is electrically conductive.

17. The downhole seal as recited in claim 15 wherein the inorganic material is selected from the group consisting of metals and metal oxides.

18. The downhole seal as recited in claim 14 wherein the strain sensor is embedded within an elastomeric element of a downhole seal assembly operable to provide a seal between a production tubing and a wellbore.

19. The downhole seal as recited in claim 14 wherein the circuitry identifies changes in an electrical property of the strain sensor as an indication of the strain being experienced by the strain sensor.

20. The downhole seal as recited in claim 14 wherein the circuitry identifies changes in a magnetic property of the strain sensor as an indication of the strain being experienced by the strain sensor.

* * * * *